US00PP31152P2

(12) United States Plant Patent
Pineau

(10) Patent No.: US PP31,152 P2
(45) Date of Patent: Dec. 3, 2019

(54) ***HIBISCUS* PLANT NAMED 'MINSYBLE9'**

(50) Latin Name: *Hibiscus syriacus*
Varietal Denomination: MINSYBLE9

(71) Applicant: Patrick Pineau, Saint Mathurin sur Loire (FR)

(72) Inventor: Patrick Pineau, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 15/999,225

(22) Filed: Aug. 16, 2018

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./226, 257
See application file for complete search history.

(56) References Cited

PUBLICATIONS

UPOV-PLUTO: Plant Variety Database, Apr. 11, 2019, citation for 'minsyble9'. 1 page. (Year: 2018).*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Hibiscus* cultivar named 'MINSYBLE9' is disclosed, characterized by large, dark violet-blue flower with a deep red basal blotch. Flower buds are uniquely dark Violet-Blue. Plants are erect and well branched. The new variety is a *Hibiscus*, normally produced as an outdoor garden or container plant.

2 Drawing Sheets

Figure 1:
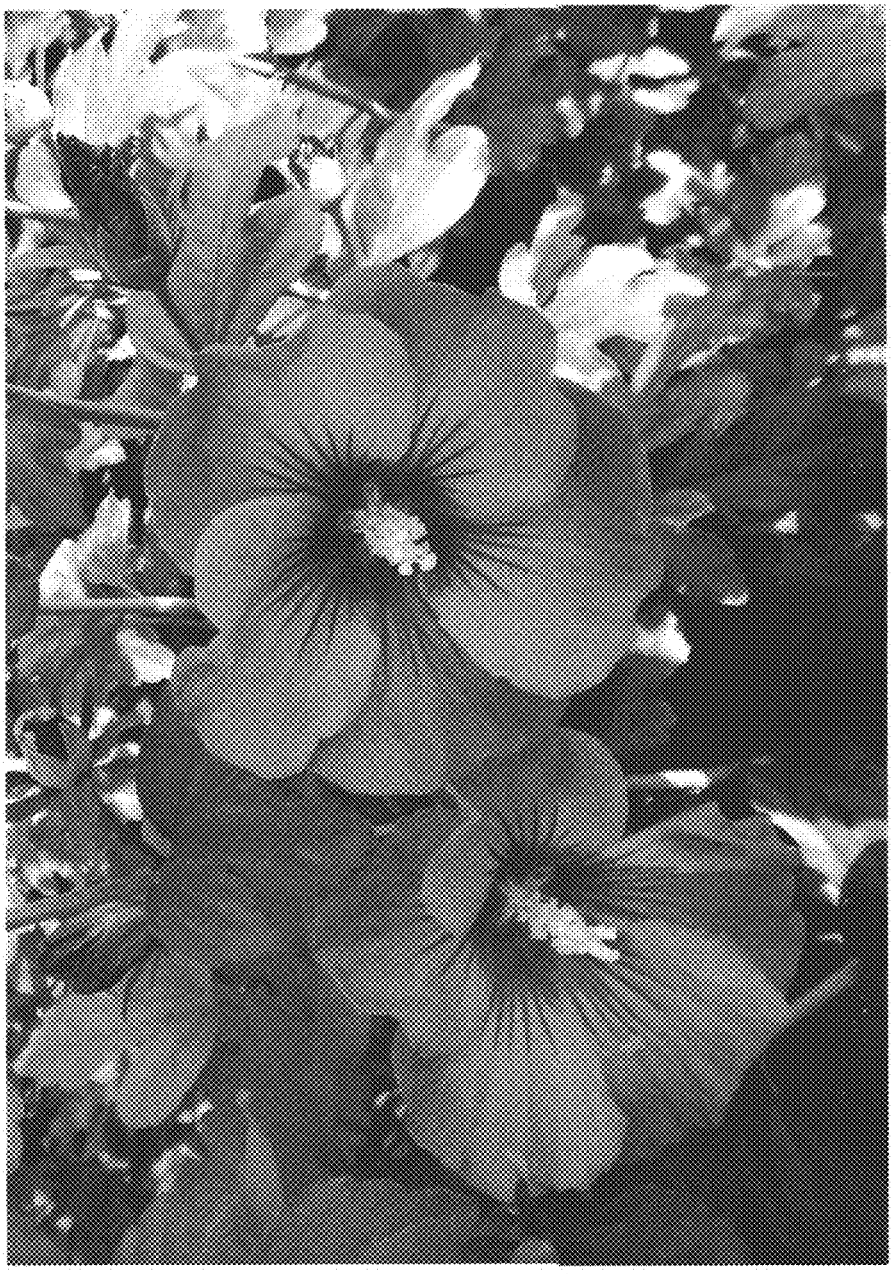

Latin name of the genus and species: *Hibiscus syriacus*.
Variety denomination: 'MINSYBLE9'

BACKGROUND OF THE INVENTION

The new *Hibiscus* cultivar is a product of a planned breeding program conducted by the inventor, Patrick Pineau. The objective of the breeding program was to look for a new dark blue large flower with healthy foliage. The cross resulting in this new variety was made during 2009.

The seed parent is the unpatented proprietary *Hibiscus syriacus* referred to as '11647'. The pollen parent is the unpatented *Hibiscus syriacus* 'Minultra'. The new variety was identified and selected as a potentially interesting selection in September 2012. Selection was made at a commercial nursery in La Menitre, Maine Et Loire, France.

Asexual reproduction of the new cultivar 'MINSYBLE9' was first performed in January 2013 in La Menitre, Maine Et Loire, France, by grafting semi-hardwood cuttings onto common rootstock. Subsequent propagation has shown that the unique features of this cultivar are stable and reproduced true to type in 6 successive generations.

SUMMARY OF THE INVENTION

The cultivar 'MINSYBLE9' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSYBLE9' These characteristics in combination distinguish 'MINSYBLE9' as a new and distinct *Hibiscus* cultivar:

1. Dark violet blue flower.
2. Very deep blue flower bud.
3. Erect plant form.
4. Well branched plants.
5. Dark green foliage.

PARENT COMPARISON

Plants of the new cultivar 'MINSYBLE9' are similar to plants of the seed parent variety in most horticultural characteristics, however, plants of the new cultivar 'MINSYBLE9' differ in the following;

1. 'Minsyble9' is more vigorous and produces more branches than the seed parent.
2. 'Minsyble9' has a larger and flatter flower than the seed parent.
3. 'Minsyble9' has a dark violet blue flower, compared to the purple flower of the seed parent.
4. 'Minsyble9' produces a dark blue bud flower, flower buds of the seed parent are violet.
5. 'Minsyble9' has a dark violet basal blotch on petal, the seed parent produces a red basal blotch.

Plants of the new cultivar 'MINSYBLE9' are similar to plants of the pollen parent variety in most horticultural characteristics, however, plants of the new cultivar 'MINSYBLE9' differ in the following;

1. 'Minsyble9' is more vigorous and produces more branches than the pollen parent.
2. 'Minsyble9' has darker violet blue flowers than pollen parent.

3. 'Minsyble9' has a dark blue bud flower, compared to the medium blue bud of the pollen parent.
4. 'Minsyble9' has a dark violet basal blotch on the petal, the pollen parent has a red-violet basal blotch.
5. 'Minsyble9' has a dark blue edge blush on the petal, the pollen parent has a light blue petal margin.
6. Petal arrangement of 'Minsyble9' is very overlapping, compared to slighting overlapping petals of the pollen parent.

COMMERCIAL COMPARISON

Plants of the new cultivar 'MINSYBLE9' can be compared to the variety *Hibiscus* 'Minsygrb11', unpatented. These varieties are similar in most horticultural characteristics however, 'MINSYBLE9' differs in the following:

1. 'Minsyble9' has a darker violet blue flower than 'Minsygrb11'.
2. 'Minsyble9' has a dark blue bud flower, compared to the medium blue flower bud of 'Minsygrb11'.
3. 'Minsyble9' has a smaller sized flower than 'Minsygrb11'.
4. 'Minsyble9' has more attractive green foliage than 'Minsygrb11' during the all the Summer season.

BRIEF DESCRIPTION OF THE PHOTOGRAPHS

The accompanying photograph in FIG. 1 illustrates in full color typical flowers of 'MINSYBLE9'.

Figure 2:
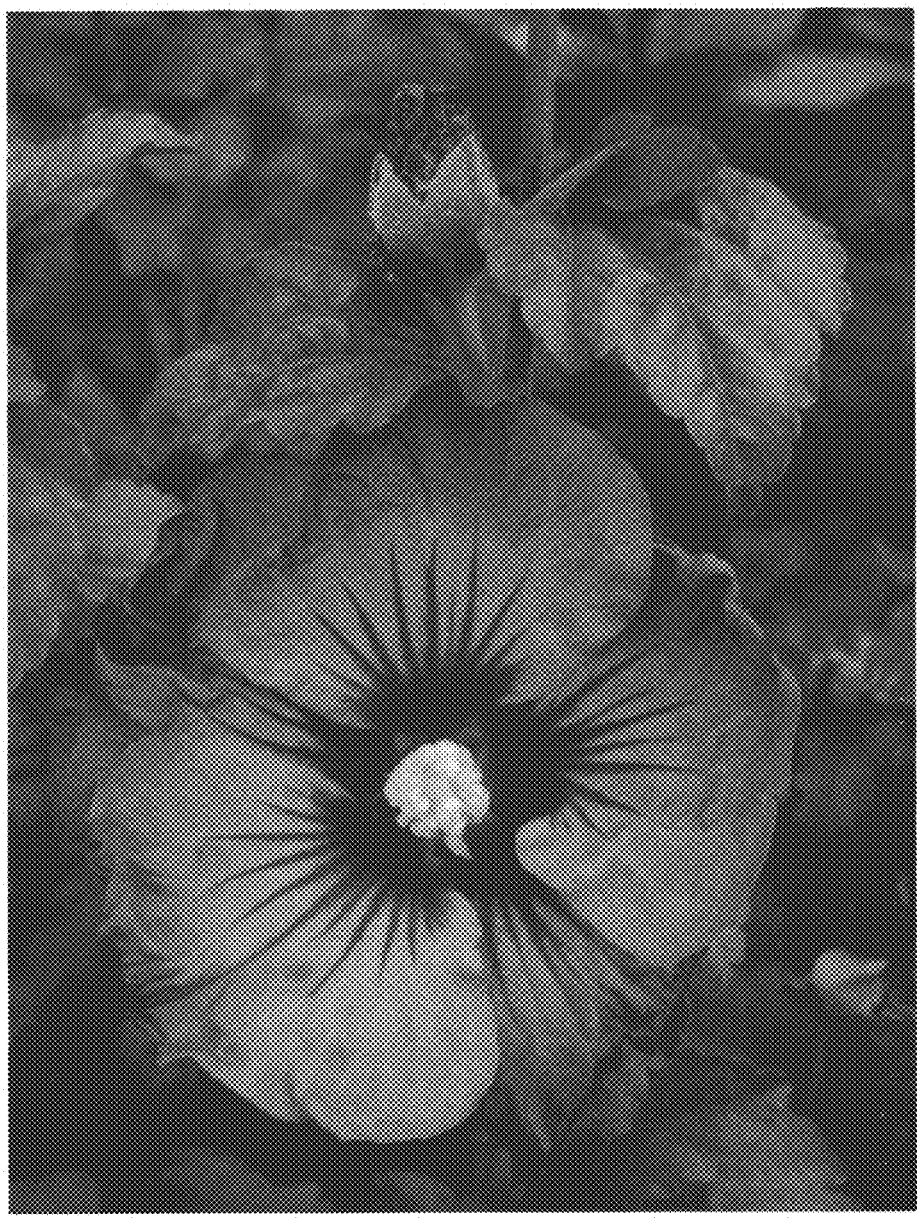

FIG. 2 illustrates in full color a typical flower and bud of 'MINSYBLE9'.

Age of the plant photographed is approximately 2 years. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'MINSYBLE9' plants grown outdoors in La Minetre, France under natural lighting. Measurements were taken during the Summer of 2018. The plants were approximately 3 years old planted in the ground. The growing temperature ranged from approximately −5° C. to 32° C. Measurements and numerical values represent averages of typical plant types.

Botanical classification: *Hibiscus syriacus* 'MINSYBLE9'

PROPAGATION

Time to Initiate Roots: 20 days at approximately 25° C.

Root Description: Fibrous, medium root thickness. Tan/brown in color, not effectively measured with a color chart.

PLANT

Plant type: Perennial shrub.

Age of Plant Described: Approximately 3 years old.

Growth Habit: Erect deciduous flowering shrub.

Height: About 100 cm.

Spread: About 35 cm.

Length of Primary Lateral Branches: 90 cm.

Quantity of Lateral Branches: 8.

Characteristics of Primary Lateral Branches:

*Diameter.*—4 mm.

*Color.*—RHS Yellow-Green 147C.

Internode length: 5 cm.

FOLIAGE

Leaf:

*Arrangement.*—Alternate.

*Quantity.*—Approximately 25 per branch.

*Average Length.*—9 cm.

*Average Width.*—6 cm.

*Shape of blade.*—Ovate.

*Apex.*—Acute.

*Base.*—Obtuse.

*Margin.*—Crenate.

*Texture of top surface.*—Glabrous.

*Texture of bottom surface.*—Rough.

*Color: Young foliage upper side: RHS Green* 137D. Young foliage under side: RHS Green 137D. Mature foliage upper side: RHS Green 137B. Mature foliage under side: RHS Green 137C.

*Venation.*—Type: Pinnate. Venation color upper side: RHS Green 137A. Venation color under side: RHS Green 137A.

*Petiole.*—Length: 1.4 cm. Diameter: 0.15 cm. Color: RHS Yellow-Green 147C.

FLOWER

Natural flowering season: July to September.

Flower type and habit: Solitary, rotate.

*Single, double, multiplex.*—Single.

*Petals overlapping.*—Very overlapping.

Rate of flower opening: 1 to 2 days from bud to fully opened flower.

Flower Longevity on Plant: 1 to 2 days.

Persistent or Self-Cleaning: Self-cleaning.

Bud:

*Shape.*—Ovate.

*Length.*—3 cm.

*Diameter.*—1.5 cm.

*Color.*—RHS Violet-Blue N92A.

Flower size:

*Diameter.*—10 cm.

*Depth.*—3 cm.

Petals:

*Quantity.*—5.

*Arrangement.*—Rotate.

*Length.*—5 cm.

*Width.*—6 cm.

*Shape.*—Orbicular to broad deltate.

*Apex.*—Rounded, very slightly undulate.

*Base.*—Obovate.

*Margin.*—Entire.

*Texture, upper and lower surfaces.*—Glabrous.

*Color.*—Fully opened, upper and lower surfaces: RHS Violet-Blue 92A to 93C with edge blush Violet-Blue 93B. Color basal blotch: RHS Violet-Blue N79A. Ratio of basal blotch/petal size: 1/3. Feathering color: RHS Violet-Blue N79A. Feathering size: 1.5 to 2 cm and abundant.

Sepals:
*Quantity.*—4 to 5.
*Length.*—2 cm.
*Width.*—1 cm.
*Shape.*—Ovate.
*Margin.*—Entire.
*Color.*—RHS Green 138A.
Peduncles:
*Length.*—4 cm.
*Diameter.*—0.3 cm.
*Angle.*—About 45° to the lateral branch.
*Strength.*—Strong.
*Texture.*—Slightly pubescent.
*Color.*—RHS Green 138A.
Fragrance: None.

REPRODUCTIVE ORGANS

Stamens:
*Number.*—50.
Anthers:
*Shape.*—Dorsifixed, broad kidney-shaped.
*Length.*—0.3 cm.
*Pollen color.*—RHS Yellow 4D.
*Pollen amount.*—Abundant.
Pistil:
*Number.*—1.
*Length.*—3.5 cm.
*Style.*—Length: 3 cm. Color: Near RHS White 155C.
*Stigma.*—Color: Near RHS White 155C.

OTHER CHARACTERISTICS

Seeds and fruits: Moderate quantity of flat crescent seeds. About 5 mm long, 3 mm wide. Color: RHS Greyed-Brown 199C.
Disease/pest resistance: Neither resistance nor susceptibility to normal diseases and pests of *Hibiscus syriacus* have been observed.
Temperature tolerance: Low temperature tolerance to at least USDA Zone 4, high temperature tolerance to at least 40° C.

What is claimed is:

1. A new and distinct cultivar of *Hibiscus* plant named 'MINSYBLE9' as herein illustrated and described.

* * * * *